(12) United States Patent
Keech

(10) Patent No.: US 6,392,416 B1
(45) Date of Patent: May 21, 2002

(54) ELECTRODE INTEGRITY CHECKING

(75) Inventor: Ray Keech, Huntingdon (GB)

(73) Assignee: ABB Kent Taylor Limited, Stonehouse (GB)

( * ) Notice: Subject to any disclaimer, the term of this patent is extended or adjusted under 35 U.S.C. 154(b) by 0 days.

(21) Appl. No.: 09/581,829

(22) PCT Filed: Dec. 24, 1998

(86) PCT No.: PCT/GB98/03912

§ 371 Date: Aug. 10, 2000

§ 102(e) Date: Aug. 10, 2000

(87) PCT Pub. No.: WO99/34174

PCT Pub. Date: Jul. 8, 1999

(30) Foreign Application Priority Data

Dec. 24, 1997 (GB) .............................................. 9727360

(51) Int. Cl.[7] ........................ G01N 27/416; G01R 27/26
(52) U.S. Cl. ...................................... 324/438; 324/665
(58) Field of Search ................................ 324/438, 439, 324/442, 444, 658, 663, 664, 665, 667, 679, 683; 73/861.17

(56) References Cited

U.S. PATENT DOCUMENTS

| | | | | | |
|---|---|---|---|---|---|
| 3,664,951 | A | * | 5/1972 | Armstrong | 204/232 |
| 3,896,373 | A | * | 7/1975 | Zelby | 324/439 |
| 3,965,738 | A | * | 6/1976 | Watanabe | 73/861.17 |
| 4,119,909 | A | * | 10/1978 | DeBerry | 324/439 |
| 4,204,427 | A | * | 5/1980 | Gothe et al. | 324/665 |
| 4,326,318 | A | * | 4/1982 | DeBruin et al. | 204/412 |
| 4,510,516 | A | * | 4/1985 | Bartelink | 257/296 |
| 4,820,973 | A | * | 4/1989 | Alvarez | 324/611 |
| 4,884,576 | A | * | 12/1989 | Alt | 607/18 |
| 4,969,363 | A | * | 11/1990 | Mochizuki | 73/861.17 |
| 5,351,558 | A | * | 10/1994 | Horn et al. | 73/861 |
| 5,426,984 | A | * | 6/1995 | Rovner et al. | 73/861.17 |

* cited by examiner

Primary Examiner—Safet Metjahic
Assistant Examiner—Vincent Q. Nguyen
(74) Attorney, Agent, or Firm—Larson & Taylor, PLC

(57) ABSTRACT

Impedance between potential sensing electrodes of a high impedance meter is measured by applying a ramp waveform through a capacitor coupled to one of the electrodes to generate a substantially constant current, a measure of impedance being obtained by comparing this to the potential developed across the electrodes when a different current is flowing.

24 Claims, 7 Drawing Sheets

ELECTRODE INTEGRITY CHECKING

BACKGROUND OF THE INVENTION

1. Field of the Invention

The present invention relates to the verification of electrode integrity in a measuring instrument, particularly an instrument having a high input impedance, such as an electromagnetic flowmeter or a pH or redox or other chemical (or bio-chemical) probe-type meter.

2. Description of the Related Art

It has been proposed to measure resistance between electrodes by injecting a constant current from a constant current source. This method works, but has the drawback that a complex circuit is required to inject the constant current.

EP 336 615 discloses some alternative methods in which a signal is injected by means of a capacitor. A drawback of these methods is that there are constraints imposed on the timing of injection and sampling of the signal (specifically, it is essential for pulses to be injected at the beginning of each half cycle), and it may be difficult to obtain accurate results due to the somewhat irregular shape of the voltage waveform produced by the injected signal.

SUMMARY OF THE INVENTION

The invention aims to alleviate the above drawbacks and provide an arrangement in which a reliable measurement of electrode resistance can be obtained from a relatively simple circuit.

In a first aspect, the invention provides a method of obtaining an in situ measure of impedance (or conductivity) between potential sensing electrodes of a meter having a high input impedance, the method comprising applying a substantially linear voltage ramp waveform to a capacitor coupled to one of the electrodes to generate a substantially constant current, and deriving a measure of impedance (or conductivity) by comparing the potential developed across the electrodes while the constant current is flowing to the potential developed across the electrodes when no current, or a different current, is flowing.

Throughout this specification, reference is made to potential sensing electrodes; it will be appreciated that potential must be measured between two reference points. One of these reference points may be an earthing point or some contact with a solution rather than a conventional "electrode" of the meter in question (for example, a pH or reference electrode). In the specification and claims, the term "potential sensing electrode" is intended to encompass any point from which a potential can be sensed; the invention extends to measurements between a single electrode and a solution using a suitable reference point.

An advantage of using a capacitor to inject the current is that complex switching arrangements are not required to isolate the electrodes from the impedance measuring circuitry when the potential across the electrodes is to be measured; conventional resistance measuring circuitry is liable to interfere with measurement of potential as the electrodes can typically source only a small current. Another advantage of the method is that, because the current is injected for a discrete period of time, the measurement has an opportunity to stabilise, enabling a reliable reading to be obtained without complex circuitry or correction required; this can be contrasted with pulsed measurement of impedance.

Preferably, a plurality of measures of potential are obtained while the current is injected. This enables measurement to be averaged over a period of time, which may enable noise to be cancelled or readings to be averaged to provide greater accuracy, and can provide surprisingly improved accuracy as compared to pulsed single measurements. Surprisingly, if only two readings are taken during the duration of current injection, significantly greater accuracy and consistency of results may be obtained, as the measurement is less susceptible to transients.

Preferably a measure of potential is obtained after a predetermined (relatively short) delay after commencement of injection of current. This enables the apparatus to settle, and allows any (small) stray capacitances between the electrodes to be effectively charged.

It will be understood that by substantially linear is meant that, within the limits of experimental accuracy required, the current generated by the ramp is within a desired tolerance range while the measurement is made. High input impedance is meant an impedance sufficient to ensure that the potential measured across the electrodes is not significantly (within the limits of experimental accuracy required) affected by connection of the potential sensing circuitry; ideally the impedance will be at least 1M ohm, and typically 10M ohms, 100M ohms or higher. By small current is meant a current that is typically at most a few micro amps, but may be many orders of magnitude lower (less than 1 micro amp, less than 100 nA, 10 nA or even less).

The method preferably further comprises obtaining a measure of the potential across the electrodes to derive therefrom a measure of a physical property related to the potential, said measure of potential being obtained by potential measuring means having a high input impedance without disconnecting said capacitor from said electrode.

In one preferred application, the physical property is flow rate, the method being employed in an electromagnetic flowmeter. In another preferred application, the physical property is pH, the method being employed in a pH meter. In a similar manner to a pH meter, other chemical (or bio-chemical) conditions may be sensed, for example in a redox potential meter. In both cases, the measure of impedance can be used to detect conditions such as fouled or faulty electrodes, broken wiring, absence of fluid and the like.

The method preferably includes comparing the measure of impedance to at least one threshold, and signalling at least one suspected fault condition in dependence on the results of the comparison.

The ramp waveform may be generated by any of a number of conventional ramp voltage generators.

A preferred arrangement which has the benefit of being simple and cost effective to implement is to couple the input of the capacitor to the junction between a series resistor-capacitor circuit, the potential across the combination being switched between two potentials, the time constant of the circuit being greater than the measurement period.

Alternatively, a more complex ramp synthesiser, for example based on a digital to analogue convertor or conventional linear ramp generator may be used.

The invention extends to both method and apparatus aspects, and it will be appreciated that preferred features of the method may be applied to the apparatus, and vice versa.

In a first apparatus aspect, the invention provides sensing apparatus for a meter arranged to derive a measure of a physical property from a measure of potential across sensing electrodes, the sensing circuit comprising a potential measuring circuit having a high input impedance and inputs arranged for connection to the electrodes and means for obtaining a measure of the impedance of the electrodes comprising a capacitor coupled between one of said inputs and means for generating a substantially linear ramp voltage so that the ramp voltage generates a substantially constant current through the electrode impedance, the apparatus further including means for deriving a measure of impedance based on the difference in potential across the electrodes when the substantially constant current is supplied and when no current, or a different value of current is supplied.

Preferably, the apparatus includes a capacitor coupled to each input; in this way, the absolute potential of the electrodes relative to the sensing circuit can be left floating.

The apparatus preferably further includes means for comparing the measure of impedance to at least one threshold and means for signalling a suspected fault condition based on the results of the comparison.

The sensing circuit may be employed in a pH meter including a pH sensing electrode, th sensing apparatus and an output circuit arranged to provide a calibrated measure of pH based on the measured electrode potential. The output circuit may comprise additional circuitry supplied with the output of the potential measuring circuit, or may be integrated therewith, the potential measuring circuit providing an appropriately scaled output signal.

The calibrated measure need not be individually calibrated for a particular apparatus, but may be scaled appropriately based on a general relationship between measured potential and pH for meters of a similar design.

As mentioned above, another preferred application of the invention is in an electromagnetic flowmeter, and in particular in a flowmeter having low power consumption, such as a battery-powered flowmeter.

In such an application, the apparatus preferably further includes control means arranged to control application of current to field generating coils of the flowmeter and to control application of the ramp voltage to the capacitor to enable measurements of both flow and electrode impedance to be obtained.

Preferably, also, the apparatus is arranged to apply a magnetic field to the fluid while said substantially constant electrode current is applied, and to obtain samples of electrode potential in the presence of the magnetic field and of the substantially constant current, and in the presence of the substantially constant current alone. This may enable determination of both flowrate and electrode impedance, without requiring prolonged application of an electromagnetic field; in this way, power consumption may be reduced, as application of the magnetic field typically requires significantly more power than application of the substantially constant electrode current.

The method may be adapted for use with a flowmeter.

Most preferably, the method comprises applying a pulsed magnetic field to the fluid during application of said substantially constant electrode current and obtaining successive first, second and third values of electrode potential respectively before, during, and after application of the pulsed magnetic field, all during application of the substantially constant electrode current. In this way, variations in the substantially constant current can be compensated for by averaging. In addition, the inventors have found that, unexpectedly, better results may be obtained if a relatively short magnetic pulse is applied than if a short electrical pulse is applied. Furthermore, application of the magnetic field generally requires substantially more power than application of the electrode current, so application of a short magnetic field and a longer electric field may reduce power consumption.

To improve results further, further values of the electrode potential may be obtained in the absence of said substantially constant electrode current, preferably at least one further value in the absence of a magnetic field, and another further value in the presence of a magnetic field. Preferably, magnetic pulses of alternating plurality are employed; this may reduce hysteresis effects. In addition (independently) electrode currents of alternating polarity may be employed; this may reduce the effects of polarisation. In both cases, references to alternating polarity (particularly in the case of currents of alternating polarity) may be extended to include groups of pulses of alternating polarity. For example, a sequence of pulse elements (which may have varying magnitudes or signs) may be followed by a similar sequence in which the polarity of each or at least the majority of the pulse elements is reversed; this may still inhibit long-term polarisation without every consecutive element alternating in polarity.

The invention may be employed to provide an EM flowmeter with an 'empty pipe detector', which is required to ensure the flowrate output is controlled, usually driven down scale, under this empty or partially full pipe condition.

The invention may also be applied to flowmeters having a permanent magnet to generate a magnetic field.

BRIEF DESCRIPTION OF THE DRAWINGS

An embodiment of the invention will now be described, by way of example, with reference to the accompanying drawings in which.

DETAILED DESCRIPTION OF THE PREFERRED EMBODIMENTS

Figure 1:
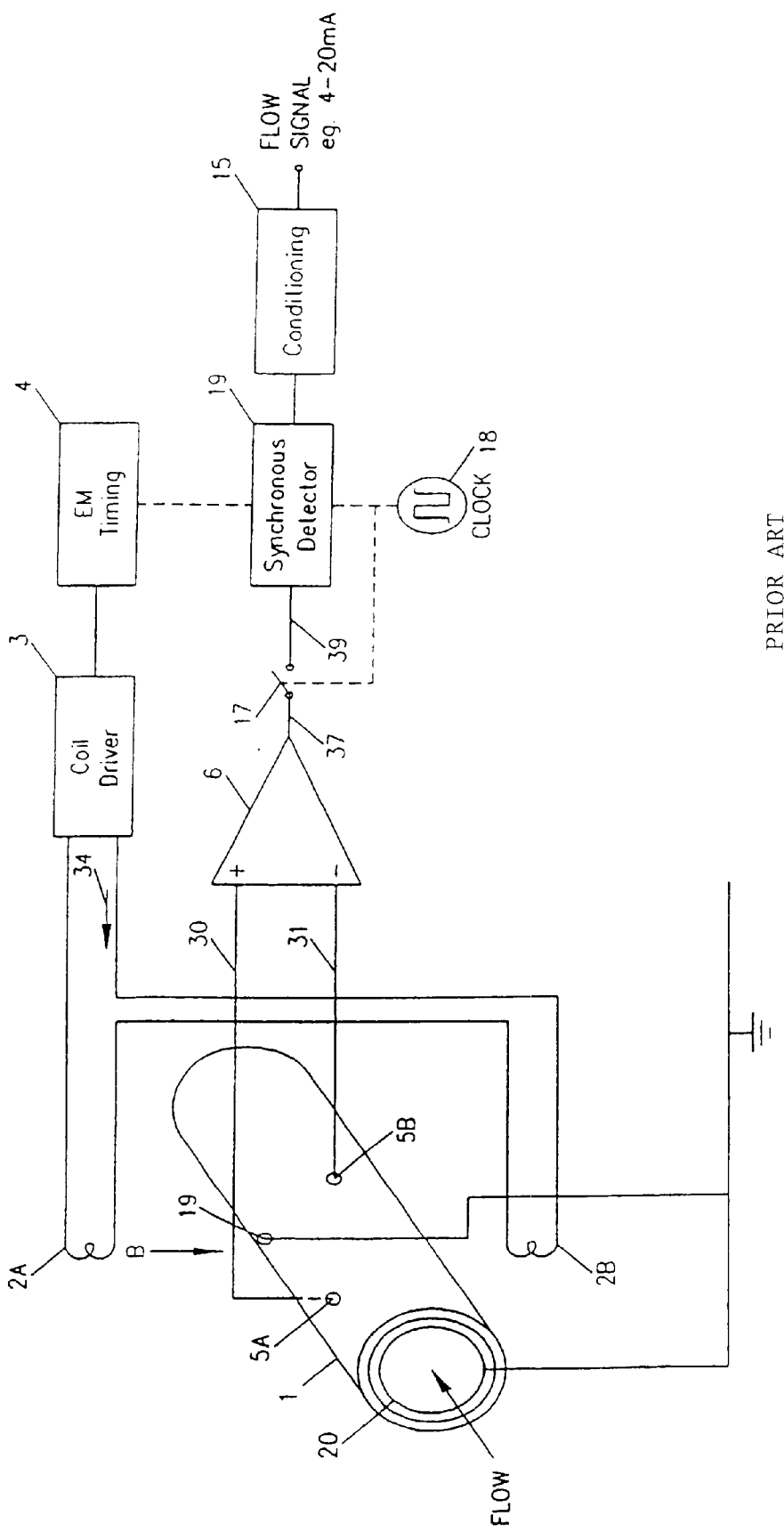
FIG. 1 is a schematic illustration of a conventional electro magnetic flowmeter.
Figure 2:
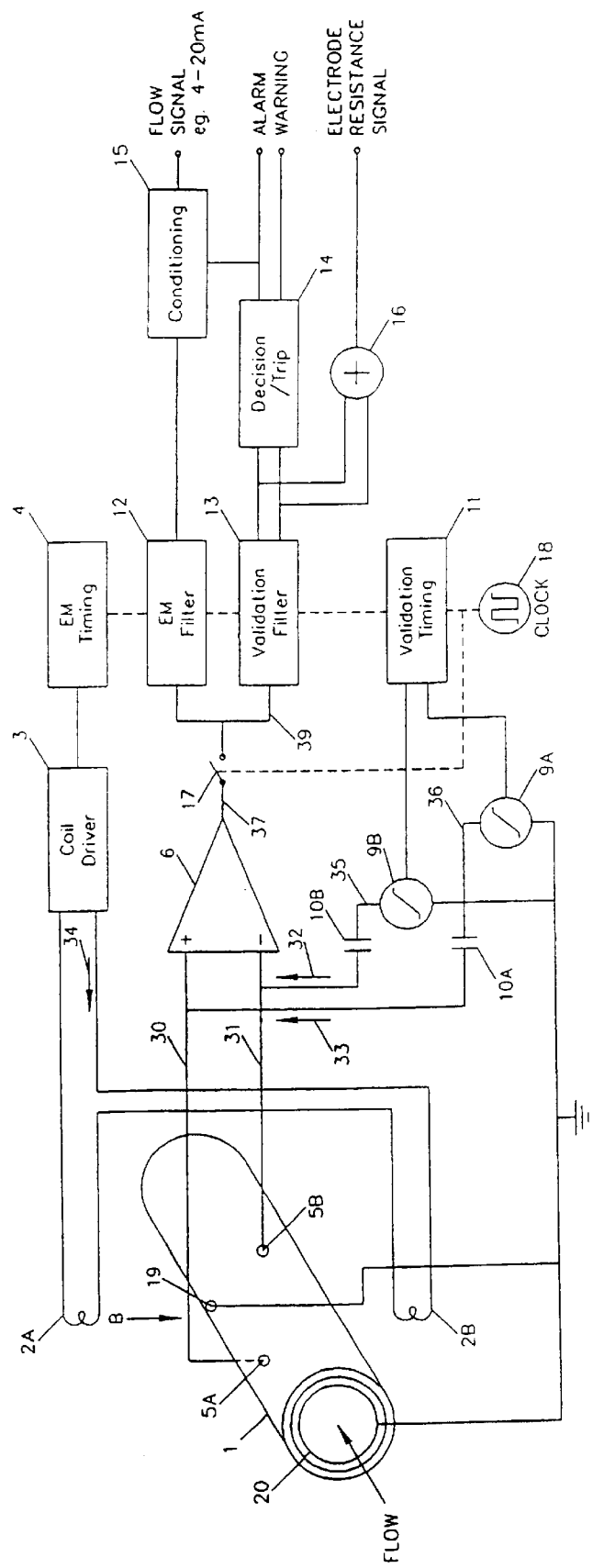
FIG. 2 is a block diagram showing a flowmeter according to a first embodiment of the present invention.

The first embodiment of the present invention is shown in FIG. 2. The fluid flow is passed through a pipe 1, which contains an insulating lining 20 if the pipe is itself conductive. The signal measuring electrodes 5A, 5B are mounted on opposite sides of the pipe 1. A fluid earthing electrode 19 is present in this embodiment, but can be omitted; if only two electrodes are used, then the potential across the electrodes can be measured when a current is injected if earthing of the fluid is not required, for example in some battery-powered applications. An alternating magnetic field B is generated by coils 2A, 2B, excited by an excitation or coil driver circuit 3. The coils 2A, 2B and its associated magnetic circuit are designed such that a magnetic field is generated perpendicular to the fluid flow and the electrode plane. An electrical excitation is generated by a voltage ramp generator 9A which is applied to one of the electrode 5A via capacitor 10A. The capacitor value for 10A is selected to be of a suitably low value, e.g. 100 F, so that the linear voltage ramp generator 9A causes a small, approximately constant, current to flow through capacitor 10A and hence into the electrode 5A and the fluid. Similarly a second ramp generator 9B generates a constant current through capacitor 10B and electrode 5B. This constant current, which is proportional to the rate of change of voltage with time (dV/dt), flows through the equivalent resistance, which is the equivalent circuit of the electrode, surface coating, fluid conductivity and its wiring, represented by an equivalent resistance Re causing a voltage to be developed, hereinafter known as the 'electrode resistance signal'. This voltage is measured and amplified, with the induced EM flow signal, by the differential amplifier 6 fed from electrodes 5A, 5B. EM excitation timing is defined by timing circuit 4 with the timing of the electrical ramp generator excitation is defined by timing circuit 11. The output voltage, consisting of the EM flow signal and 'electrode resistance signal' is fed to two filters 12, 13. The input to these filters can be continuous time or sampled time, in the latter case the sampling switch 17, controlled by a master clock 18 provides this function. The output of filter 12 is proportional to flowrate, filter 13 is proportional to 'electrode resistance signal'. The output of filter 12 is then further processed by conditioning circuit 14 to generate the desired output signal such as 4–20 mA. The output of validation filter 13, produces 2 output signals corresponding to the electrode resistance of electrode 5A to ground and electrode 5B to ground.

These two signals can be used independently or jointly in a decision block/trip 15 to determine if the electrodes circuit is working correctly, which includes electrodes 5A, 5B, coating on 5A, 5B, lining coatings, wiring, fluid level, or damage. If a fault is developed such that the electromagnetic flowmeter will not operate correctly, then an alarm signal is generated, which will drive the flow indication to a safe condition, usually downscale. The decision/trip circuit 14 can also generate a warning signal to indicate a problem is present or developing, such as electrode coating. The two electrode resistance signals are also summed to generate a combined electrode resistance signal, which could be output to indicate fluid conductivity.

The separation of the electromagnetic and electrode resistance signals is further detailed below.

Figure 4:
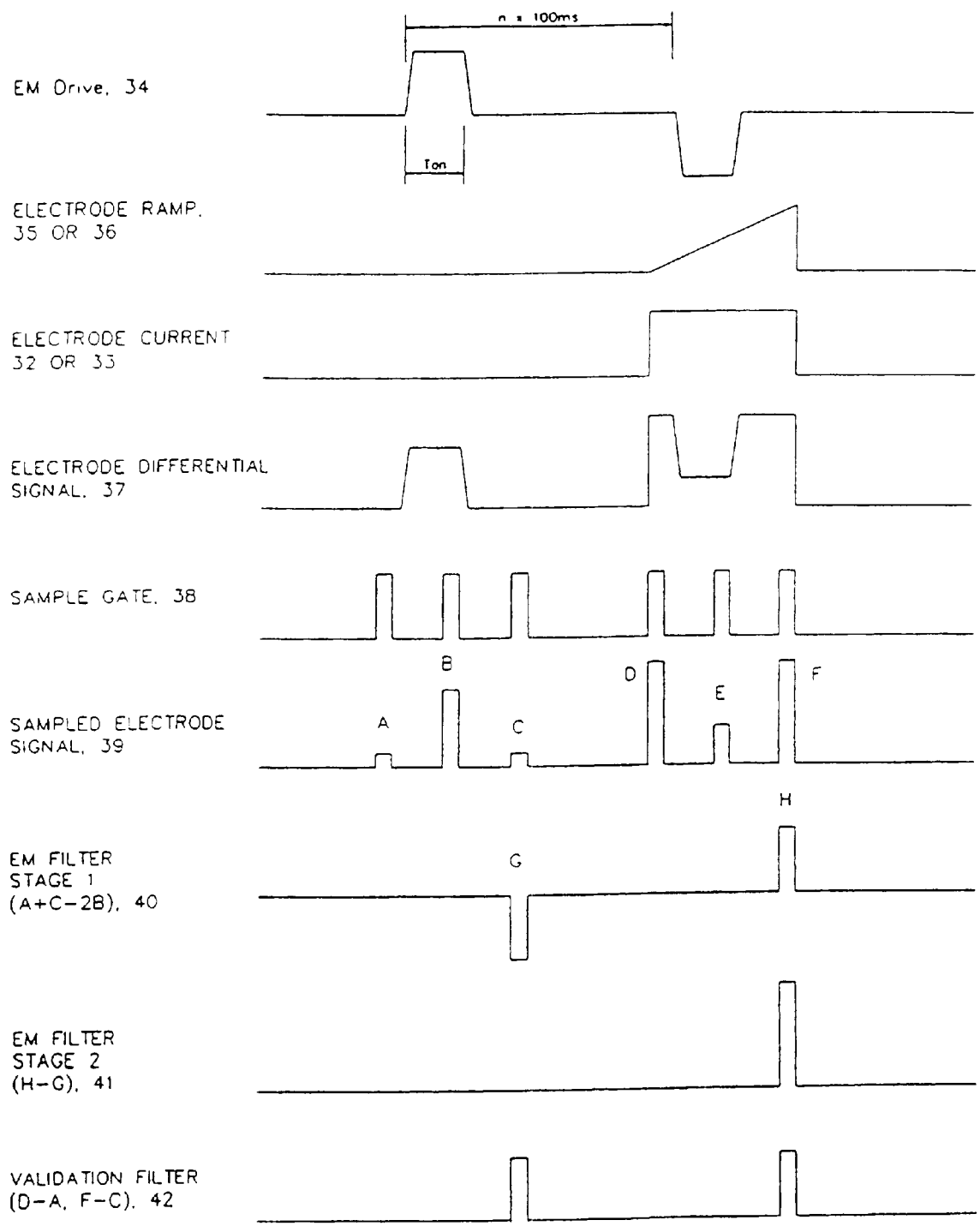
FIG. 4 comprises timing charts for explaining the operation of the embodiment shown in FIGS. 2 and 3.

FIG. 4 is a diagram illustrating the timing associated with a low powered embodiment of this invention. The electromagnetic drive, usually a constant current 34 is pulsed in one direction, off, then in the opposite direction, then off. This generates a corresponding magnetic flux inside the meter, which generates a voltage of a similar waveform shape. An voltage ramp signal from either 9A or 9B generates a corresponding signal 35 or 36. The resulting constant currents into the electrodes 32 or 33. The effective impedance of the electrode, its circuitry and the fluid generate the corresponding electrode resistance signal, this has similar waveform shape to 32 or 33, but is superimposed onto the electromagnetically induced flow signal similar in shape to 34. The sum is illustrated in the electrode differential signal 37.

Figure 3:
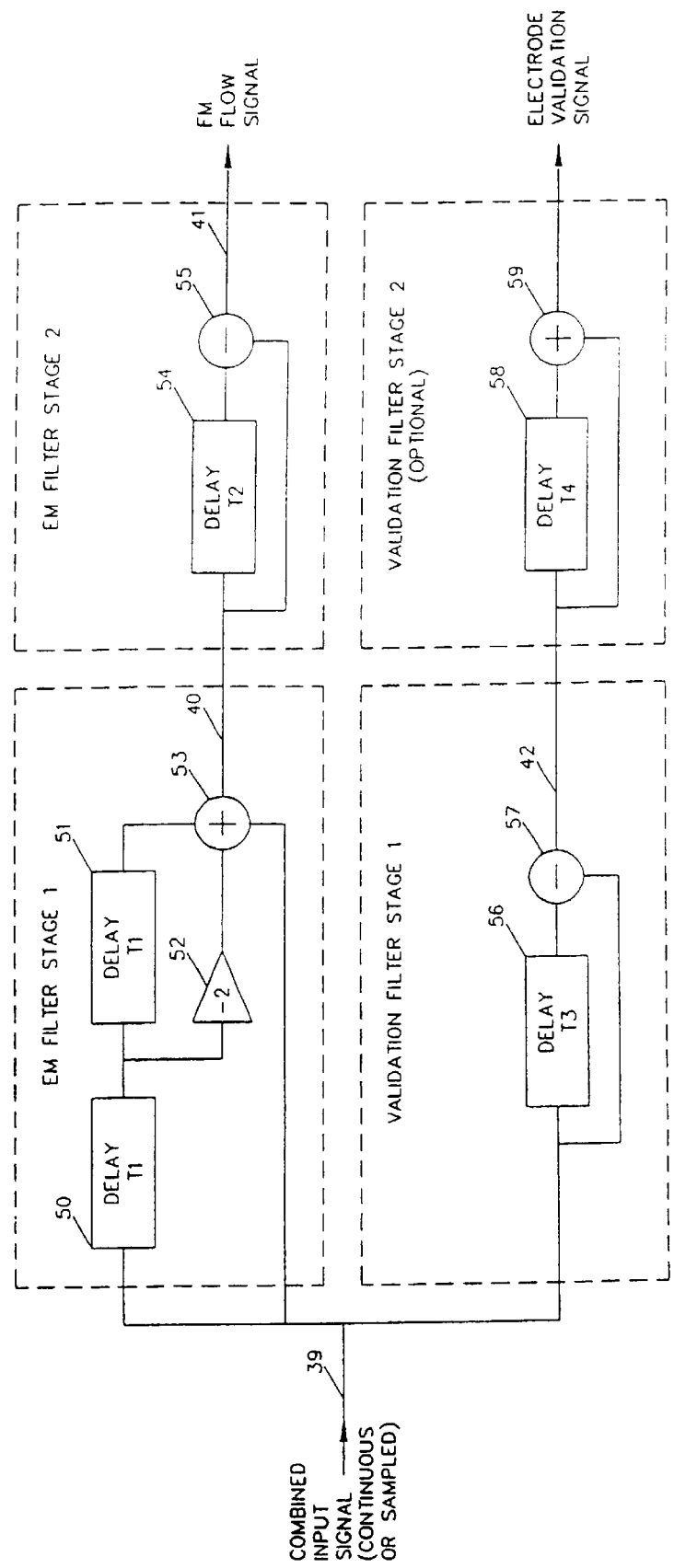
FIG. 3 schematically illustrates the filtering used to extract the flow signal and electrode resistance signals.

In order to extract the separate flow and validation signals the combined signals are processed by filters 12 & 13, which are illustrated in more detail in FIG. 3. Here the combined signal is sampled using sample gate 17, signal 37, producing sampled signal 39. Use of a sampled waveform simplifies processing and understanding although the principal below operates for a continuous analogue signal. To extract the electromagnetic signal a series of Finite Impulse Response (FIR) comb filters are used. The first stage comb filter illustrated performs an A+C−2B function on the waveforms identified on trace 39, generating an output signal 40. It will be noticed that this processing has removed all trace of the electrode resistance signal. The reason for using such processing is to rejects electrochemical and flow noise which tends to be predominantly low frequency in nature, often with a 1/f frequency characteristic. The EM filter stage 2 performs a waveform H−G operation, effectively demodulating the drive signal and giving the desired flow signal, which is not affected by the superimposed electrode resistance signal.

To extract the electrode resistance signal the combined signal 39 is fed to Validation comb filter stage 1, which performs the function illustrated by D−A and F−C, giving signal 42. These two signals may be used individually or combined in the illustrated Validation filter stage 2 to give one signal which is (D−A)+(F−C).

For the comb filters in FIG. 3 to operate correctly the delay times T1, T2, T3 & T4 must be set to match the excitation waveform. By defining the delays such that:

$$T2, T3 = n \times 100 \text{ ms}$$

where n is a positive integer
then this circuit also rejects all mains bourne interference, at both 50 Hz or 60 Hz and all harmonics of these frequencies, on the recovery of both the EM signal and the electrode resistance signal. This technique is based on the invention patented by the author in UK Patent GB 2 271 639. To match the electromagnetic excitation $$T1 = T\text{on}.$$

Similarly then it follows that to give the desired function $$T4 = 2 \times T\text{on}$$

In the case of the above analysis it has only been assumed that one electrode circuit is driven at a time from either 9A or 9B. Clearly through symmetry it is possible on one electromagnetic drive cycle to drive say 9A, then on the next cycle drive 9B. That way its is possible to essentially continuously validate each individual electrode.

An advantage of this invention is that the electrode resistance measurement is made using capacitive coupling with a low value capacitor 10A, 10A, which has a benefit of not loading the electrode circuit with any resistive losses. The very high input resistance of differential amplifier 6 is not degraded, ensuring that when electrodes do become slightly coated and resistive, or metering low conductivity fluids such that the flowrate reading is not shunted and accuracy affected.

Figure 5:
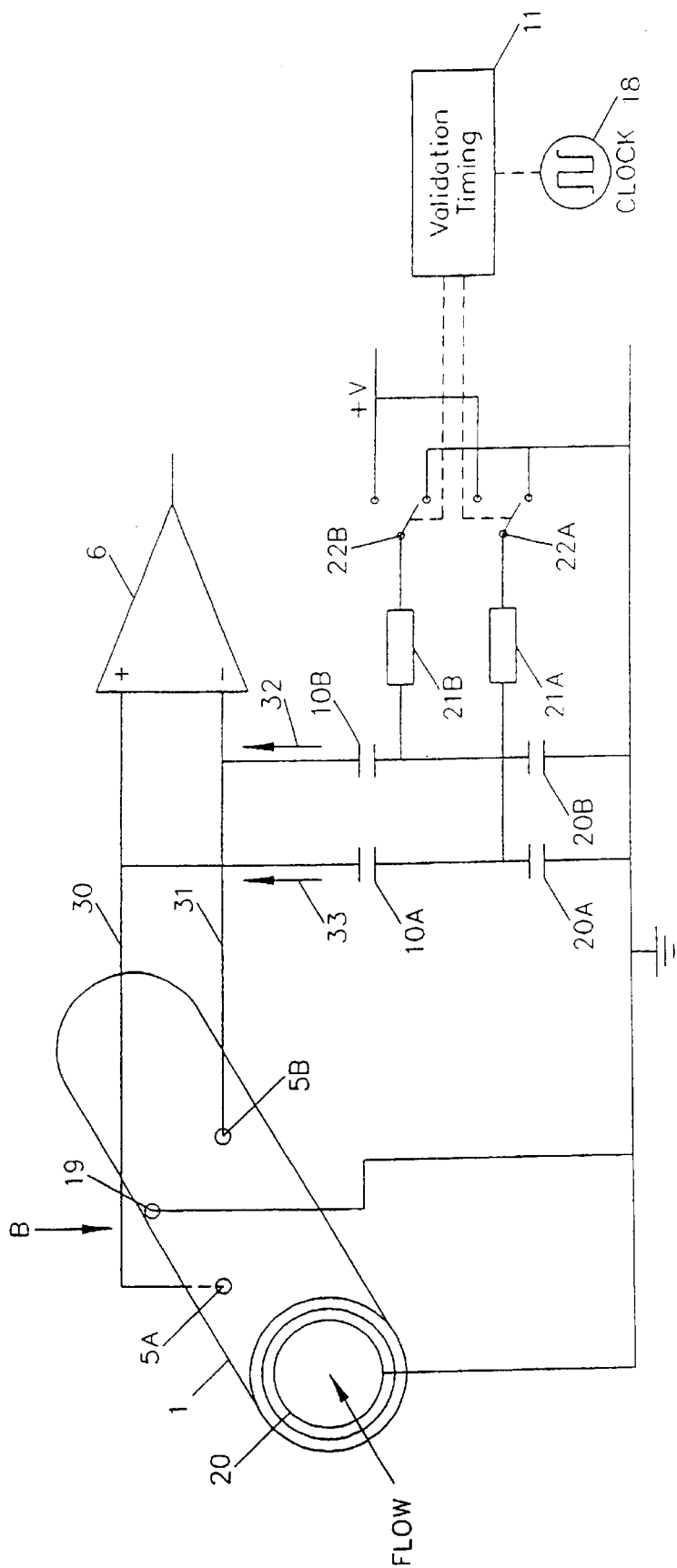
FIG. 5 is a block diagram of a second, simplified embodiment.

In a further embodiment of this invention the voltage ramp generators 9A and 9B are approximated by a simple resistor capacitor combination as illustrated in FIG. 5. With this arrangement an exponential ramp is generated by a voltage step from switches 22A, 22B fed to resistor 21a, 21b and capacitors 20a, 20b. This exponential is sufficiently close to linear ramp that the signal processing of FIG. 3 rejects the unwanted cross signal components. This arrangement has a further advantage that it the capacitor combination of 10 and 20 act as a radio frequency interference filter, reducing susceptibility to unwanted radio frequencies.

Figure 6:
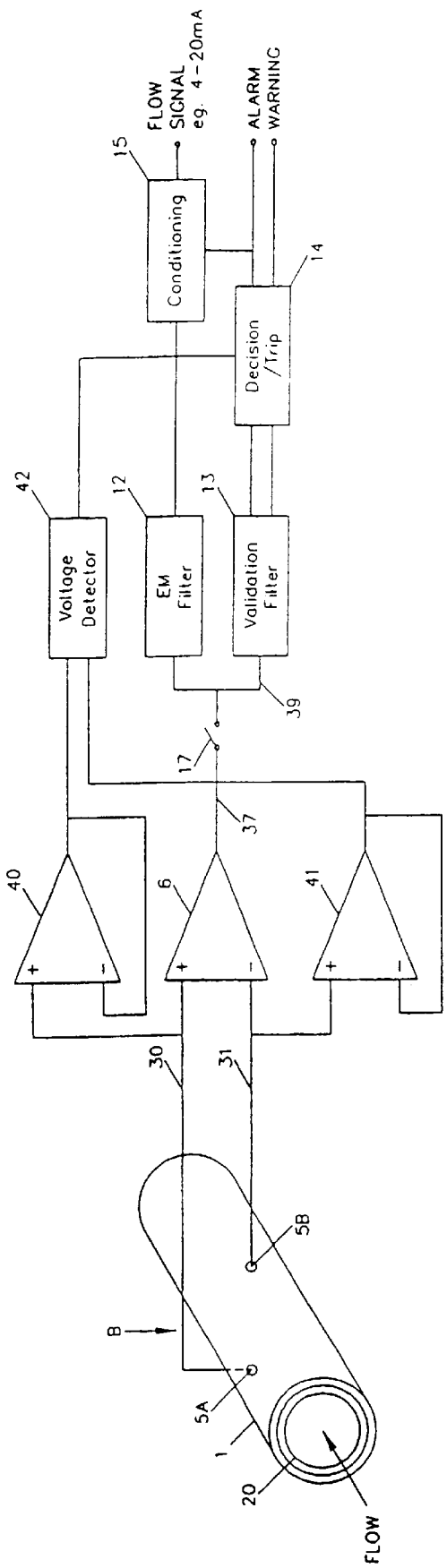
FIG. 6 depicts a third embodiment incorporating a voltage monitor.
Figure 7:
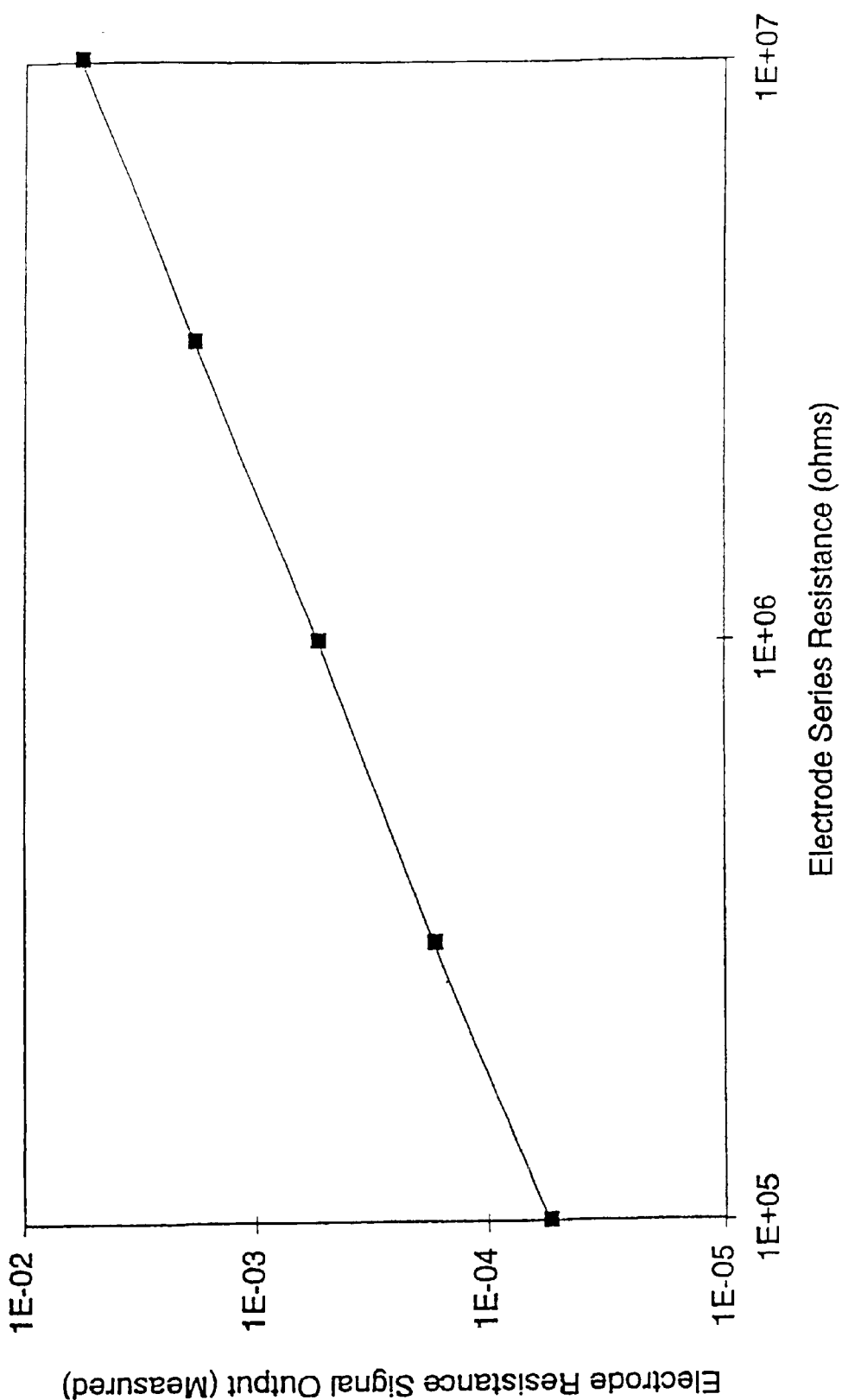
FIG. 7 is a graph indicating a relationship between electrode resistance and a measured output signal.

In a further embodiment of this invention, illustrated in FIG. 6, the electrode voltages are buffered 40, 41 then fed to a voltage monitoring detector circuit 42 which measures the voltage on each electrode. If an electrode develops an open circuit or the pipe 1 is empty then the constant current from capacitors 10A, 10B can attempt to generate a high signal or voltage level which could overload later circuitry, such an Analogue to Digital converter that would be required for subsequent processing in digital form. Such a detector 42 will enable saturation/limiting of any processing to be detected.

The invention has been described above in the context of an electromagnetic flowmeter. As mentioned above, the invention may be applied to other meters such as pH meters. In such a case, simpler control circuitry is required, as it is not necessary to provide drive current at appropriate times for field coils. In a pH meter, for example, all that is required of the control circuitry is to apply the ramp waveform and measure the difference between the potential across the electrodes in the presence of this waveform and in its absence; this will give a measure of the electrode impedance. The pH can be derived in the normal manner from the potential measured in the absence of the ramp waveform.

The above description concentrates on measuring impedance. It will be appreciated that conductivity, or any other related parameter can be derived in a similar manner; conductivity is merely the reciprocal of impedance. All references to obtaining a measure of impedance are intended to encompass any such related quantities.

What is claimed is:

1. A method of obtaining an in situ measure of impedance between potential sensing electrodes of a meter having a high input impedance, the method comprising applying a substantially linear voltage ramp waveform to a capacitor coupled to one of the electrodes to generate a substantially constant current, and deriving a measure of impedance by comparing a potential developed across the electrodes while the constant current is flowing to a potential developed across the electrodes when no current, or a different current, is flowing.

2. A method according to claim 1, wherein the ramp waveform is generated by coupling an input of a capacitor to a junction between a series resistor-capacitor circuit, the potential across the combination being switched between two potentials, and the time constant of the circuit being greater than a measurement period for deriving said measure of impedance.

3. A method according to claim 1, wherein the ramp waveform is generated by a voltage synthesiser.

4. A method according to claim 1, wherein a plurality of measures of potential are obtained while said constant current is generated.

5. A method according to claim 1, wherein a measure of potential is obtained after a predetermined delay after commencement of generation of the constant current.

6. A method according to claim 1, wherein the physical property is pH, the method being employed in a pH meter.

7. A method according to claim 1, including performing a comparison by comparing the measure of impedance to at least one threshold, and signaling at least one suspected fault condition in dependence on a result of the comparison.

8. A method according to claim 1, further comprising obtaining a measure of the potential across the electrodes to derive therefrom a measure of a physical property related to the potential, said measure of potential being obtained by using potential measuring means having a high input impedance and without disconnecting said capacitor from said electrode.

9. A method according to claim 8, wherein the physical property is flow rate, the method being employed in an electromagnetic flowmeter.

10. Sensing apparatus for a meter arranged to derive a measure of a physical property from a measure of potential across sensing electrodes, the sensing circuit comprising a potential measuring circuit having a high input impedance and inputs arranged for connection to the electrodes and means for obtaining a measure of the impedance between the electrodes comprising a capacitor coupled between one of said inputs and means for generating a substantially linear ramp voltage so that the ramp voltage generates a substantially constant current through the electrodes, the means for obtaining a measure of impedance being arranged to derive said measure based on the difference in potential across the electrodes when the substantially constant current is supplied and when no current, or a different value of current is supplied.

11. Apparatus according to claim 10 including a capacitor coupled to each input.

12. Apparatus according to claim 10 further including means for comparing the measure of impedance obtained by the means for obtaining the measure of impedance to at least one threshold and means for signalling a suspected fault condition based on the results of the comparison.

13. A pH meter including a pH sensing electrode, sensing apparatus according to claim 10, and an output circuit arranged to provide a calibrated measure of pH based on the electrode potential measured by the sensing apparatus.

14. A pH meter according to claim 13 including control means arranged to apply said ramp voltage to obtain said measure of electrode impedance and means for detecting a fault condition based on the measure of impedance, the meter being arranged to provide an output of a pH measurement or an indication that pH measurement may be invalid.

15. Sensing apparatus according to claim 10 for use in an electromagnetic flowmeter, the flowmeter comprising field coils, the sensing apparatus including control means arranged to control application of current to the field generating coils of the flowmeter and to control application of the ramp voltage to the capacitor so that measurements of both flow and electrode impedance can be obtained.

16. Apparatus according to claim 15, arranged to apply a magnetic field to a fluid while said substantially constant current is applied, and to obtain samples of electrode potential in the presence of the magnetic field and of the substantially constant current, and in the presence of the substantially constant current alone.

17. An electromagnetic flowmeter comprising field generating coils, potential sensing electrodes and sensing apparatus according to claim 15.

18. An electromagnetic flowmeter according to claim 17, further comprising output means arranged to provide a measure of flow rate as said measure of the physical property or an indication that flow rate measurement may be invalid.

19. An electromagnetic flowmeter according to claim 17 including means arranged to provide an output signifying that a pipe through which flow is being measured by said flowmeter may be empty or partially empty.

20. An electromagnetic flowmeter according to claim 17, arranged to produce an output signifying zero flow on detection of an impedance signifying that a pipe through which flow is being measured by said flowmeter is empty.

21. A method of obtaining measurements of flow of a fluid and electrode impedance in an electromagnetic flowmeter having field generating coils and potential sensing electrodes, the method comprising applying a substantially linear voltage ramp waveform to a capacitor coupled to one of the flowmeter sensing electrodes to generate a substantially constant current, deriving a measure of impedance by comparing the potential developed across the electrodes while said constant current is flowing to the potential developed across the electrodes when no current, or a different current, is flowing, and deriving a measure of flow from the potential developed across the electrodes when no current is flowing, or based on a plurality of values of potential measured at a plurality of different values of said substantially constant current.

22. A method according to claim 21, wherein obtaining measures of flow and impedance comprises applying a pulsed magnetic field to the fluid during application of said substantially constant current and obtaining successive first, second and third values of electrode potential respectively before, during, and after application of the pulsed magnetic field, all during application of the substantially constant current.

23. A method according to claim 22 wherein magnetic pulses of alternating polarity are employed.

24. A method according to claim 21 wherein a plurality of values of said substantially constant current are employed, including currents of alternating polarity.

* * * * *